(12) United States Patent
Sugiura

(10) Patent No.: US 8,231,883 B2
(45) Date of Patent: *Jul. 31, 2012

(54) SILVER-BASED INORGANIC ANTIMICROBIAL AGENT AND METHOD FOR PREPARING THE SAME

(75) Inventor: Koji Sugiura, Naogya (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/320,501

(22) PCT Filed: May 12, 2010

(86) PCT No.: PCT/JP2010/058001
§ 371 (c)(1),
(2), (4) Date: Nov. 14, 2011

(87) PCT Pub. No.: WO2010/131667
PCT Pub. Date: Nov. 18, 2010

(65) Prior Publication Data
US 2012/0064131 A1    Mar. 15, 2012

(30) Foreign Application Priority Data
May 15, 2009  (JP) ................. 2009-118164

(51) Int. Cl.
  *A01N 59/26*  (2006.01)
  *A01N 25/34*  (2006.01)
  *A01P 1/00*  (2006.01)
(52) U.S. Cl. ...................... 424/400; 424/604
(58) Field of Classification Search ............ None
See application file for complete search history.

(56) References Cited

U.S. PATENT DOCUMENTS
7,771,738 B2 * 8/2010 Sugiura et al. ............... 424/405

FOREIGN PATENT DOCUMENTS

| JP | 2-267137 A | 10/1990 |
|---|---|---|
| JP | 3-083905 A | 4/1991 |
| JP | 4-275370 A | 9/1992 |
| JP | 5-017112 A | 1/1993 |
| JP | 2000-290007 A | 10/2000 |
| JP | 2008-074778 A | 4/2008 |
| JP | 2008-074781 A | 4/2008 |
| WO | WO 2009/044477 A1 | 4/2009 |
| WO | WO 2009/044478 A1 | 4/2009 |

OTHER PUBLICATIONS

International Search Report, PCT/JP2010/058001, Jun. 22, 2010
Ota et al., "Low-Thermal-Expansion KZr2(PO4)3 Ceramic",Journal of the Ceramic Association, 1987 vol. 95, No. 5, pp. 531-537.

* cited by examiner

*Primary Examiner* — Scott Long
*Assistant Examiner* — Sarah Alawadi
(74) *Attorney, Agent, or Firm* — Birch, Stewart, Kolasch & Birch, LLP

(57) ABSTRACT

Disclosed are a powder of a silver-based inorganic antimicrobial agent with superior dispersability or water permeability, composed of silver-supporting hexagonal zirconium phosphate, and an antimicrobial product and a water processing material using the silver-based inorganic antimicrobial agent powder. The silver-based inorganic antimicrobial agent containing hexagonal zirconium phosphate crystals, which has a particle size distribution to enable easy handling as a powder and contribute to exhibition of antimicrobial properties, can be prepared by a preparation method including wet-heating zirconium carbonate. When the silver-based inorganic antimicrobial agent wherein particles with a size of 10 μm to 100 μm are 90% or more on a volume basis is kneaded into resin products, since aggregation or the like may not occur and the silver-based inorganic antimicrobial agent can be easily exposed on the surface of molded articles, antimicrobial effects are thus readily exhibited on the surface.

6 Claims, 2 Drawing Sheets

SILVER-BASED INORGANIC ANTIMICROBIAL AGENT AND METHOD FOR PREPARING THE SAME

TECHNICAL FIELD

The present invention relates to a silver-based inorganic antimicrobial agent containing hexagonal zirconium phosphate crystals, which has a particle size distribution to enable easy handling as a powder, readily exhibit antimicrobial properties and allow smooth water permeation, and a method for preparing the same. The silver-based inorganic antimicrobial agent of the present invention may be used as a variety of antimicrobial products or water processing materials.

BACKGROUND ART

Zirconium phosphates include amorphous zirconium phosphates and crystalline zirconium phosphates including a 2-dimensional layered structure or a 3-dimensional network structure. Of these, hexagonal zirconium phosphates having a 3-dimensional network structure exhibit superior heat resistance, chemical resistance, radiation resistance and low thermal expansion properties and the like and are thus being researched for use as immobilizers for radioactive waste, solid electrolytes, gas adsorbing/separating agents, catalysts, antimicrobial agent raw materials, and fillers with low thermal expansion properties and the like. In particular, the silver-based inorganic antimicrobial agents obtained by supporting silver ions on hexagonal zirconium phosphates exhibit superior antimicrobial effects as well as excellent durability or long-lasting effects, are not readily discolored during resin processing and are superior in terms of product safety and may be thus utilized for processing into a variety of types of resins or applications.

Various hexagonal zirconium phosphates are currently known. For example, $NaZr_2(PO_4)_3$, $CaZr_4(PO_4)_6$, $KZr_2(PO_4)_3$ and the like are disclosed in PTL 1 or NPL 1.

Known methods for synthesizing zirconium phosphates include a calcination method in which synthesis is carried out by mixing raw materials in a dry manner and then calcining the mixture at 1,000° C. or higher using a calcining furnace (for example, see PTL 2 and PTL 4), a hydrothermal method in which synthesis is carried out by mixing raw materials in water or mixing raw materials containing water and then heating under pressure, and a wet method in which synthesis is carried out by mixing raw materials in water and then heating at normal pressure (for example, see PTL 3), etc.

Among these synthesis methods, in the calcination method, it is not easy to uniformly mix raw materials and it is therefore difficult to obtain zirconium phosphate with a homogeneous composition with such a method. In addition, since crystallization by calcination causes the formation of agglomerated materials by calcination, it is necessary to grind these materials to convert the same into a powder with a specific particle size. However, since zirconium phosphates having high crystallinity have high hardness, abrasion of a grinding apparatus or contamination by abraded materials readily occurs. It is difficult to obtain particles having a particle size distribution with the narrow range disclosed in the present invention, since the shape or particle size of the ground crystals may not be controlled.

Meanwhile, a wet method or a hydrothermal method enables homogeneous zirconium phosphate salt powders to be easily obtained. However, the obtained powder is mainly a particulate crystalline powder with a size of 1 μm or less. To obtain a zirconium phosphate salt powder having a particle size higher than 1 μm at a high yield, it is necessary to age materials with a low concentration in an aqueous solution for a long period of time. For this reason, in practice, there are technical and economical difficulties. In addition, a method of screening and filtering out large particles from particulates obtained by a conventional wet method or hydrothermal method involves great costs and is not economical. That is, neither the preparation method of hexagonal zirconium phosphate particles having a particle size distribution with a narrow range, used for the present invention, nor the special characteristics thereof, are known.

Meanwhile, an antimicrobial agent in which antimicrobial metal ions are supported on these zirconium phosphate salts has been suggested. For example, PTL5 discloses the following Formula (1).

$$M^1{}_aA_bM^2{}_c(PO_4)_2 \cdot nH_2O \quad (1)$$

(In Formula (1), $M^1$ represents a metal ion selected from silver, copper, zinc, tin, mercury, lead, iron, cobalt, nickel, manganese, arsenic, antimony, bismuth, barium, cadmium and chromium, A represents at least one ion selected from an alkali metal ion, an alkaline earth metal ion, an ammonium ion and a hydrogen ion, $M^2$ represents a tetravalent metal, n represents a value satisfying $0 \leq n \leq 6$, a and b are positive numbers, c and d satisfy $c=2$ and $d=3$, provided that $la+mb=1$, and c and d satisfy $c=1$, $d=2$, provided that $la+mb=2$, in which l is the valence of $M^1$ and m is the valence of A.)

Ions such as silver, copper, zinc, tin, mercury, lead, iron, cobalt, nickel, manganese, arsenic, antimony, bismuth, barium, cadmium and chromium have been known for a long time as antimicrobial metal ions that exhibit antimold properties, antimicrobial properties, and antialgal properties. As antimicrobial agents possessing antimold properties, antimicrobial or antialgal properties, organic support antimicrobial agents in which antimicrobial metal ions are supported on an ion exchange resin, a chelate resin or the like, and inorganic antimicrobial agents in which antimicrobial metal ions are supported on a clay mineral, an inorganic ion exchanger or a porous body have been suggested. In particular, silver-based inorganic antimicrobial agents in which silver ions among antimicrobial metal ions are supported on an inorganic compound have properties of improved safety, long-lasting antimicrobial effects, and superior heat resistance as compared to a silver nitrate aqueous solution, thus having few restrictions on an application method, a storage method, a disposal method and applications as well as currently being applied to a variety of products. However, silver ions are unstable when exposed to heat and light and are immediately reduced into silver metals, thus having a problem of stability such as discoloration over a long period of time. Depending on the type of inorganic compounds to support the silver ions, the performance of the obtained silver-based inorganic antimicrobial agents varies and the antimicrobial agents frequently have restrictions.

Silver ions-supporting zirconium phosphate salts are known as materials which are chemically and physically stable and exert antimold properties and antimicrobial properties for a long period of time. Commonly, zirconium phosphate salts can be readily obtained as particulates and are thus easily applied to fibers, coatings and the like and are utilized in a variety of applications. However, in a case where a processed antimicrobial agent such as water processing materials is needed to be separated from water, or for a use in coatings or films with a specific thickness where crude particulate antimicrobial agents exhibit superior dispersibility, as compared to particulate antimicrobial agents and thus enable easy handling, conventional particulate zirconium phosphate salt powders have a disadvantage of poor separation from water, that is, a poor water permeation property, or poor dispersibility with respect to coatings or resins. Accordingly, there is a need for solutions to this disadvantage.

CITATION LIST

Patent Literature

PTL 1: JP-A-02-267137 (JP-A denotes a Japanese unexamined patent publication application.)
PTL 2: JP-A-2000-290007
PTL 3: JP-A-05-017112
PTL 4: JP-A-03-83905
PTL 5: JP-A-04-275370
Non-Patent Literature
NPL 1: Toshitaka Ota, Iwao Yamai, "Preparation of low thermal expansion $KZr_2(PO_4)_3$ ceramic" Journal of the Ceramic Association, 1987, Vol. 95, No. 5, p 531-537.

SUMMARY OF INVENTION

Technical Problem

The object of the present invention is to provide a silver-based inorganic antimicrobial agent powder containing silver-supporting hexagonal zirconium phosphate, which exhibits excellent dispersibility or excellent water permeation properties, and water processing materials and antimicrobial products using the silver-based inorganic antimicrobial agent powder.

Solution to Problem

As a result of an intensive investigation to solve the problems, the present inventors discovered that a silver-based inorganic antimicrobial agent in which 90% or more based on volume thereof is composed of particles with a size of 10 μm to 100 μm can be obtained by supporting silver on hexagonal zirconium phosphates which are composed of coarse particles and have high crystallinity, obtained by dispersing zirconium carbonate in an aqueous solution containing at least one ion selected from an alkali metal ion, an alkaline earth metal ion and an ammonium ion, and a phosphate ion, wet-heating and aging the dispersion, and then performing dry-heating.

EXPLANATION OF REFERENCES

Figure 1:
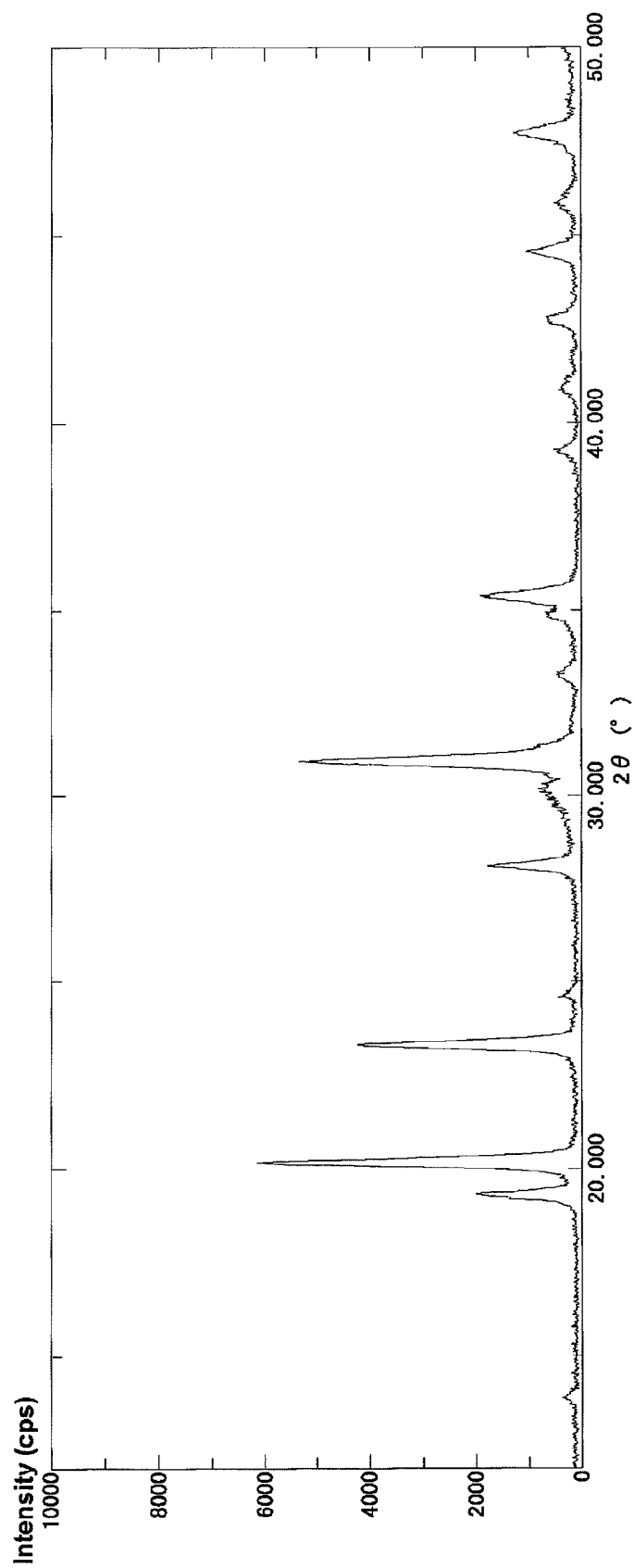
FIG. 1 is an X-ray diffraction chart illustrating silver-supporting hexagonal zirconium phosphate obtained in Example 1 using a powder X-ray diffraction apparatus.
Figure 2:
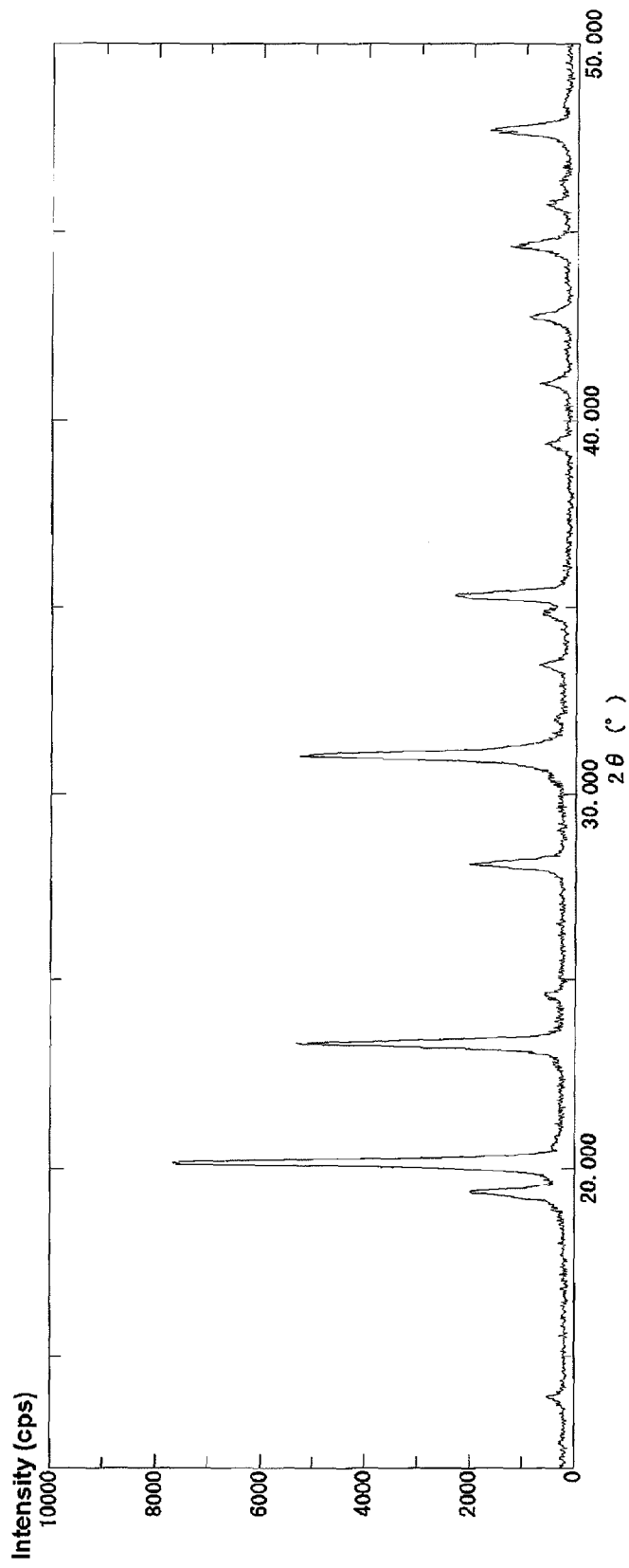
FIG. 2 is an X-ray diffraction chart illustrating silver-supporting hexagonal zirconium phosphate obtained in Comparative Example 1 using a powder X-ray diffraction apparatus.

Vertical axes in FIGS. 1 and 2 show X-ray intensity (unit: cps) in a powder X-ray diffraction measurement.
Horizontal axes in FIGS. 1 and 2 show diffraction angle 2θ (unit: °) of an X-ray.

Description of Embodiments

Hereinafter, the present invention will be described. In addition, % means % by mass.

A method for preparing zirconium phosphate salt represented by Formula (2), which is used to support silver for a silver-based inorganic antimicrobial agent of the present invention includes dispersing a zirconium carbonate powder in an aqueous solution containing at least one ion selected from an alkali metal ion, an alkaline earth metal ion and an ammonium ion, and a phosphate ion, wet-heating and aging the dispersion and performing dry-heating in this order.

$$M_b{}^*Zr_cHf_d(PO_4)_3 \cdot nH_2O \qquad (2)$$

In Formula (2), M represents at least one ion selected from an alkali metal ion, an alkaline earth metal ion, an ammonium ion and a hydrogen ion, $b^*$, c and d are values satisfying $1.75 < c+d < 2.25$, and $b^*+4(c+d)=9$ provided that M is monovalent, and $2b^*+4(c+d)=9$ provided that M is divalent, $b^*$, c and d are positive numbers, c and d are zero or positive numbers, and n is zero or a positive number of 2 or less.

In a case where M is a combination of a monovalent ion and a divalent ion, the coefficient of a is appropriately multiplied depending on a ratio of the monovalent M and the divalent M. For example, when a molar ratio of the monovalent M and the divalent M is 40/60, $b^*$ in the equation of $b^*+4(c+d)=9$ may be substituted by $(40/100+2\times(60/100))\,b^*$.

A preferred value of $b^*$ in Formula (2) varies in cases of an alkali metal ion, an ammonium ion, a hydrogen ion or an oxonium ion, and an alkaline earth metal ion. In the case of an alkali metal ion, an ammonium ion or a hydrogen ion, $b^*$ is a positive number lower than 2 and is preferably 0.7 to 1.2, and is more preferably 0.75 to 1.0. Meanwhile, in the case of an alkaline earth metal ion, $b^*$ is a positive number lower than 1 and is preferably 0.35 to 0.6 and is more preferably 0.4 to 0.5.

In Formula (2), c and d are values satisfying $1.75 < c+d < 2.25$, and $b^*+4(c+d)=9$. c is preferably higher than 1.75 and equal to or lower than 2.1, more preferably 1.85 to 2.07, yet more preferably 1.9 to 2.03. In addition, d is preferably 0.2 or less, more preferably 0.01 to 0.2, yet more preferably 0.015 to 0.15.

In Formula (2), n is preferably 1 or less, more preferably 0.01 to 0.5, yet more preferably 0.03 to 0.3. When n is higher than 2, the absolute amount of moisture contained in the silver-based inorganic antimicrobial agent powder of the present invention is high, and there is a concern that foaming and hydrolysis or the like may occur during heating or the like, when mixed with a variety of materials.

A zirconium carbonate powder, which may be used as a material for synthesizing the zirconium phosphate salt powder represented by Formula (2) and used to support silver for the silver-based inorganic antimicrobial agent of the present invention, is preferably slightly water soluble or water insoluble. Specifically, the solubility in deionized water at room temperature (20° C.) is preferably lower than 0.5 g/100 g water and more preferably lower than 0.1 g/100 g water. In addition, regarding the particle size distribution of the zirconium carbonate powder, particles with a particle size of 5 μm to 100 μm are preferably 80% or more on a volume basis of the total particles of the zirconium carbonate powder, particles with a particle size of 6 μm to 90 μm are more preferably 80% or more on a volume basis, and particles with a particle size of 7 μm to 80 μm are yet more preferably 90% or more on a volume basis. The measurement of the particle size may be preferably carried out using a laser diffraction particle size distribution meter or a centrifugal sedimentation particle size distribution meter, Coulter counter, a counting method using an electron microscope or the like. Of these, the laser diffraction particle size distribution meter is particularly preferable and the powder is preferably dispersed in water or an organic solvent and then measured to avoid the influence of aggregation.

Specific examples of zirconium carbonate include basic zirconium carbonate $2ZrO_2.CO_2.xH_2O$, zirconium bicarbonate $ZrO_2.2CO_2.xH_2O$ and zirconium carbonate $3ZrO_2.CO_2.xH_2O$ as well as double salts containing ammonium, sodium, potassium or the like (in which x represents zero or a positive number). Basic zirconium carbonate is particularly preferable. In addition, in the present invention, zirconium carbonate preferably contains hafnium and the content of hafnium is preferably 0.2% to 5%, with respect to zirconium, taking into consideration reactivity or economic efficiency.

An aqueous solution for dispersing zirconium carbonate in the present invention is an aqueous solution which contains at least one ion selected from an alkali metal ion, an alkaline earth metal ion and an ammonium ion, and a phosphate ion.

Examples of the alkali metal ion which may be used as a material for synthesizing the zirconium phosphate salt represented by Formula (2), used for supporting silver for the silver-based inorganic antimicrobial agent of the present invention include ions such as lithium, sodium, potassium, rubidium and cesium. Compounds containing these metal ions are necessarily water-soluble and useful examples thereof include chlorides, hydroxides, nitrates, sulfates, carbonates and the like. Hydroxide is preferable in that pH can be controlled by the concentration. Preferred alkali metal ions include sodium ions and potassium ions, and preferred compounds include sodium hydroxide and potassium hydroxide. In addition, examples of the alkaline earth metal ions used in the present invention include ions such as magnesium, calcium, strontium and barium. A magnesium ion or a calcium ion is preferable. In addition, as necessary for the application or the like, other transition metal ions may also be added thereto.

A molar ratio of an alkali metal ion, an alkaline earth metal ion and an ammonium ion, and zirconium carbonate (assuming that the zirconium carbonate compound is 1) used for synthesizing zirconium phosphate represented by Formula (2), used for supporting silver for the silver-based inorganic antimicrobial agent of the present invention is preferably equal to or higher than 0.3 and is lower than 0.8, more preferably equal to or higher than 0.35 and is lower than 0.75, yet more preferably equal to or higher than 0.4 and is equal to or lower than 0.7.

A phosphate ion source that may be used as a material for synthesizing the zirconium phosphate salt represented by Formula (2), used for supporting silver for the silver-based inorganic antimicrobial agent of the present invention may be any one which is ionized in water to produce a phosphate ion. Specifically, examples of the phosphate ion source include phosphoric acid, sodium phosphate, potassium phosphate and ammonium phosphate, and metaphosphoric acid, polyphosphoric acid and phosphorus pentoxide. More preferred are an alkali metal salt, an alkaline earth metal salt and an ammonium salt of phosphoric acid, or phosphoric acid, and yet more preferred is phosphoric acid. In addition, the concentration of phosphoric acid is preferably about 60% to about 85%, when it is used as a raw material. The phosphate ion is produced in an aqueous solution no matter which phosphorous compound is used Since polyphosphoric acid has a low ionization degree, none of the polyphosphoric acid present in an aqueous solution is present as a phosphate ion and ionization equilibrium is thus formed between a phosphate ion source and the phosphate ion. In addition, hydrogen phosphate ions or dihydrogen phosphate ions are simultaneously produced and form an equilibrium state, and the content ratio thereof varies depending on the pH of the aqueous solution. When the phosphate ion source is present in water, phosphate ions are necessarily produced, and an aqueous solution containing a phosphate ion source is thus the same as an aqueous solution containing a phosphate ion.

The concentration of the zirconium carbonate powder dispersed in water or an aqueous solution is not particularly limited as long as a uniform dispersion is possible. The concentration of the dispersion is preferably 5 to 50% by mass and yet more preferably 10% to 40%. When the concentration is lower than 5%, production efficiency is deteriorated and economic efficiency is thus lowered. Meanwhile, when the concentration is higher than 50%, the viscosity of a dispersion is excessively high, thus making it hard to stir and difficult to mix uniformly. A molar ratio of phosphoric acid serving as the phosphate ion source and zirconium carbonate (assuming that the zirconium compound is 1) is preferably 1.1 to 1.7, more preferably 1.2 to 1.6 and yet more preferably 1.2 to 1.5, from a viewpoint of high crystallinity.

In addition to the aforementioned conditions, the aqueous solution for dispersing the zirconium carbonate is preferably an aqueous solution which contains at least one ion selected from an alkali metal ion, an alkaline earth metal ion and an ammonium ion and has a pH of 5 to 9.

The hexagonal zirconium phosphate salt powder of crude particles can be obtained by dispersing zirconium carbonate in an aqueous solution satisfying these conditions, adding oxalates as a complexing agent thereto, and wet-heating and aging the mixture or performing dry-calcinating after aging. Since zirconium carbonate is different from zirconium phosphate crystals and enables easy control of particle size, a zirconium phosphate salt powder with a limited particle size distribution and the silver-based inorganic antimicrobial agent of the present invention can be obtained by using zirconium carbonate having a coarse particle size distribution of about 5 to 100 μm as a raw material and limiting preparation conditions such that the particle size thereof does not greatly vary during reaction with phosphoric acid.

A method for dispersing a zirconium carbonate powder in water is not limited and examples thereof include adding a zirconium carbonate powder to an aqueous solution containing at least one ion selected from an alkali metal ion, an alkaline earth metal ion and an ammonium ion, and a phosphate ion, adding water containing at least one ion selected from an alkali metal ion, an alkaline earth metal ion and an ammonium ion, and a phosphate ion to water in which a zirconium carbonate powder is dispersed, and adding, to water in which a zirconium carbonate powder is dispersed, a compound serving as an ion source thereof and the like.

After mixing raw materials, the materials are preferably stirred and aged with heating, such that they are homogeneously mixed and the reaction is uniformly performed. An aging period may be 10 minutes to 24 hours and is preferably 1 hour to 10 hours. When the materials are aged within 10 minutes, they may not be uniformly mixed and it may be difficult to obtain homogeneous zirconium phosphate with high crystallinity. Meanwhile, when the materials are stirred for 24 hours or more, there is neither a problem associated with qualities nor variation in crystallinity, etc, but economic efficiency is low.

The heating aging temperature when zirconium phosphate is prepared is preferably 40° C. or higher, and more preferably 60° C. or higher, yet more preferably 70° C. or higher. As the aging temperature increases, it is easy to obtain a hexagonal zirconium phosphate powder with high crystallinity and the aging period is shortened. The upper limit of aging temperature is 100° C. at normal pressure (1 atmosphere), but may be higher than 100° C. when pressurized. However, when the process is performed at an excessively high temperature and at an excessively high pressure, equipment costs are incurred. Accordingly, a preferred upper limit is 200° C.

In the case of wet-heating aging, crystallization can be facilitated with only wet-heating aging by adding an oxalic acid compound as a complexing agent. Examples of the oxalic acid compound include oxalic acid dihydrate, sodium oxalate, ammonium oxalate, sodium hydrogen oxalate, and ammonium hydrogen oxalate and oxalic acid dihydrate is preferred. However, in the wet-heating aging, particulate zirconium phosphate salts may be produced depending on mixing conditions of raw materials or aging conditions. For this reason, in the method for preparing hexagonal zirconium phosphate salt particles used for the present invention, crystallization is not completed only with wet-heating aging and crystallization is facilitated by dry-calcinating after wet-heating aging.

After wet-heating aging, the zirconium phosphate salt is separated by filtration, washed with deionized water and dry-heated. The washing degree is preferably such that the electrical conductivity of the filtrate is 100 to 2000 μS, and more preferably 200 to 1000 μS. When the electrical conductivity is 100 μS or lower, washing is excessive and the composition of zirconium phosphate salt is changed and the crystallinity of hexagonal zirconium phosphate salt after dry-heating may be deteriorated. When the electrical conductivity is 2000 μS or more, excess materials remain and there is a concern that hexagonal zirconium phosphate after dry-heating may be solidified or undergo deterioration in crystallinity. The heating temperature may be 650° C. to 1500° C., preferably 700° C. to 1450° C., more preferably 800° C. to 1400° C. In addition, the heating time may be 1 hour to 24 hours and is preferably 2 hours to 18 hours and more preferably 4 hours to 15 hours. A temperature elevation rate is preferably 0.1° C./min to 50° C./min until the temperature reaches a dry heating temperature. Before reaching the dry-heating temperature, a process of evaporating moisture at a temperature of 600° C. or less, preferably 60° C. to 200° C. may be added, as a drying process.

The dry-heating process may be carried out by heating with agitating or stirring to prevent formation of a skin layer on the surface of stacked powder. After heating, the powder is slightly crushed and dissociated to obtain a hexagonal zirconium phosphate salt powder with highly pure white crystals. Since the diameter of primary particles can be controlled and sintering does not easily occur, the preparation method is superior in that there is almost no necessity for grinding and screening.

Regarding the particle size of the hexagonal zirconium phosphate salt obtained by the preparation method, particles with a size of 5 μm to 100 μm are preferably 90% or more on a volume basis, particles with a size of 6 μm to 90 μm are more preferably 90% or more on a volume basis, and particles with a size of 7 μm to 80 μm are yet more preferably 90% or more on a volume basis. In addition, a median particle size based on volume is preferably 10 to 50 μm and more preferably 15 to 40 μm.

The hexagonal zirconium phosphate obtained by the preparation method is highly crystalline. The crystallinity of hexagonal zirconium phosphate may be evaluated by peak intensity derived from hexagonal zirconium phosphate crystals by powder X-ray diffraction. When measured under conditions of X-rays of 50 kV/120 mA by powder X-ray diffraction with CuKα rays, the peak intensity at about 2θ=20.2°, the peak derived from the detected hexagonal zirconium phosphates is 1,500 cps or more and is preferably 2,000 cps or more, yet more preferably 2,500 cps or more. When the peak intensity is 1,500 cps or less, sufficient crystallinity cannot be obtained and a supporting ability of silver ions is deteriorated and discoloration or the like may thus occur when kneaded into resin molded articles.

The hexagonal zirconium phosphate obtained by the preparation method is highly pure. The purity of hexagonal zirconium phosphate may be measured by confirming the presence of impurity peaks other than peaks derived from hexagonal zirconium phosphate crystals by powder X-ray diffraction and amounts of constituents contained therein by fluorescent X-ray analysis. The total of the constituents derived from hexagonal zirconium phosphate detected by fluorescent X-ray analysis is preferably 96% or more and is more preferably 99% or more.

Examples of the composition of hexagonal zirconium phosphate powder obtained by the preparation method may be provided as follows.

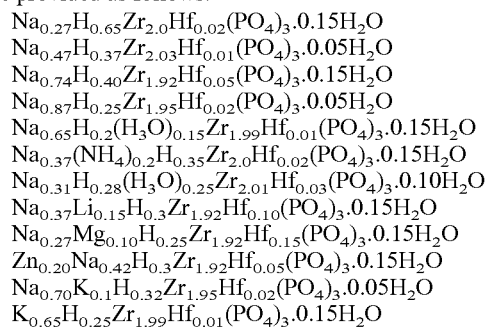

The silver-based inorganic antimicrobial agent of the present invention can be obtained by incorporating silver ions into zirconium phosphates exemplified by Formula (2) by ion exchange and thermally decomposing the same. The silver ion exchange may be readily carried out by dipping zirconium phosphate in an aqueous solution containing silver nitrate. Preferably, the aqueous solution contains a large amount of silver nitrate because this has the effect that discoloration does not readily occur, when the obtained silver-based inorganic antimicrobial agent is mixed with a resin. Meanwhile, when an excessively large amount of silver ions is present, the silver ions remain in the aqueous solution which is thus economically disadvantageous. It is preferable to use an aqueous solution containing silver nitrate in an amount in which the coefficient, b*, of Formula (2) is multiplied by 0.6 to 0.99 with respect to one mole of the zirconium phosphate compound represented by Formula (2), and more preferable to use an aqueous solution containing silver nitrate in an amount in which the coefficient, b*, of Formula (2) is multiplied by 0.7 to 0.98 with respect to one mole of the zirconium phosphate compound represented by Formula (2). The amount of zirconium phosphate dipped in the aqueous solution may be determined so that the zirconium phosphate can be uniformly mixed with the aqueous solution. Specifically, the zirconium phosphate represented by Formula (2) is preferably present in an amount of 20% by mass or less with respect to the total amount of the aqueous solution.

The aqueous solution containing silver ions may be prepared using an aqueous solution of silver nitrate in deionized water. The temperature of the aqueous solution during ion exchange may be 0 to 100° C. and preferably 20 to 80° C. Since the ion exchange is rapidly performed, a dipping time may be thus within 5 minutes and is preferably 30 minutes to 5 hours to obtain a uniform and high silver ion exchange rate.

After the silver ion exchange is completed, the resulting product is thoroughly washed with water such as deionized water and then dried to obtain the silver-based inorganic antimicrobial agent of the present invention represented by Formula (A). It is preferable that, after the silver ion exchange is completed, the resulting product is washed with water such as deionized water. Washing with water is preferably performed until the electrical conductivity of the residue reaches 500 μS or less. After washing with water, the residue is filtered, dried and thermally decomposed to obtain the silver-based inorganic antimicrobial agent represented by Formula (A).

$$Ag_aM_bZr_cHf_d(PO_4)_3 \cdot nH_2O \qquad (A)$$

(In Formula (A), M represents at least one ion selected from an alkali metal ion, an alkaline earth metal ion, an ammonium ion, a hydrogen ion and an oxonium ion, a, b, c and d are values satisfying $1.75 < c+d < 2.25$, and $a+b+4(c+d)=9$ provided that M is monovalent, and $a+2b+4(c+d)=9$ provided that M is divalent, and a, b and c are positive numbers, d is zero or a positive number, and n is zero or a positive number of 2 or less.)

In Formula (A), a satisfies $0 < a$, is preferably 0.01 or more and is more preferably 0.03 or more, and a is preferably 1 or less and is more preferably 0.6 or less. When a is lower than 0.01, an antimicrobial property may not be sufficiently exhibited.

In Formula (A), an optimal value of b may be varied depending on the type of M selected from an alkali metal ion, an ammonium ion, a hydrogen ion, and an oxonium ion. b satisfies $0 < b$ and is preferably 0.01 or more. In addition, b is lower than 1.5 and is preferably lower than 1.0 and is more preferably 0.9 or less. When the value of b is large, the antimicrobial agent of the present invention may readily cause discoloration when mixed with a resin, and, in particular, when b is 0.6 or more, discoloration may readily occur.

In Formula (A), c and d satisfy $1.75 < (c+d) < 2.2$, and c is preferably lower than 2.15 and is more preferably lower than 2.10. In addition, the lower limit is preferably 1.80 or more, is more preferably 1.85 or more, and is yet more preferably 1.90 or more. In addition, d is preferably 0.2 or less, is more preferably 0.001 to 0.15, and is yet more preferably 0.005 to 0.10.

In Formula (A), n is preferably 1 or less, more preferably 0.01 to 0.5, and yet more preferably 0.03 to 0.3. When n is higher than 2, the absolute amount of moisture contained in the silver-based inorganic antimicrobial agent is high and there is a concern that foaming, hydrolysis or the like may occur during processing or the like.

Specific examples of the silver-based inorganic antimicrobial agent represented by Formula (A) may be provided as follows.

$Ag_{0.05}Na_{0.22}H_{0.1}(H_3O)_{0.55}Zr_{2.0}Hf_{0.02}(PO_4)_3 \cdot 0.15H_2O$
$Ag_{0.17}Na_{0.32}H_{0.35}Zr_{2.03}Hf_{0.01}(PO_4)_3 \cdot 0.05H_2O$
$Ag_{0.17}Na_{0.64}H_{0.33}Zr_{1.92}Hf_{0.05}(PO_4)_3 \cdot 0.15H_2O$
$Ag_{0.45}Na_{0.47}H_{0.2}Zr_{1.95}Hf_{0.02}(PO_4)_3 \cdot 0.05H_2O$
$Ag_{0.55}Na_{0.1}H_{0.2}(H_3O)_{0.15}Zr_{1.99}Hf_{0.01}(PO_4)_3 \cdot 0.15H_2O$
$Ag_{0.05}Na_{0.32}(NH_4)_{0.2}H_{0.35}Zr_{2.0}Hf_{0.02}(PO_4)_3 \cdot 0.15H_2O$
$Ag_{0.10}Na_{0.21}H_{0.28}(H_3O)_{0.25}Zr_{2.01}Hf_{0.03}(PO_4)_3 \cdot 0.10H_2O$
$Ag_{0.17}Na_{0.20}Li_{0.15}H_{0.3}Zr_{1.92}Hf_{0.10}(PO_4)_3 \cdot 0.15H_2O$
$Ag_{0.17}Na_{0.10}Mg_{0.10}H_{0.25}Zr_{1.92}Hf_{0.15}(PO_4)_3 \cdot 0.15H_2O$
$Ag_{0.17}Zn_{0.20}Na_{0.25}H_{0.3}Zr_{1.92}Hf_{0.05}(PO_4)_3 \cdot 0.15H_2O$
$Ag_{0.45}Na_{0.27}K_{0.1}H_{0.3}Zr_{1.95}Hf_{0.02}(PO_4)_3 \cdot 0.05H_2O$
$Ag_{0.55}K_{0.1}H_{0.1}(H_3O)_{0.25}Zr_{1.99}Hf_{0.01}(PO_4)_3 \cdot 0.15H_2O$ Regarding the particle size of the silver-based inorganic antimicrobial agent represented by Formula (A), particles with a size of 10 μm to 100 μm are preferably 90% or more on a volume basis, particles with a size of 10 μm to 100 μm are more preferably 92% or more on a volume basis and particles with a size of 10 μm to 90 μm are yet more preferably 92% or more on a volume basis. In addition, a median particle size based on volume is preferably 10 to 50 μm, and is more preferably 12 to 48 μm in that the processability of the antimicrobial agent into a variety of resin products is excellent and processing defects do not readily occur. When the median particle size is 10 μm or less, separation of the particles from the aqueous solution after being used for water treatment may be deteriorated and it is difficult to synthesize particles with a size of 100 μm or more.

The form in which the silver-based inorganic antimicrobial agent is used is not particularly limited and may be suitably mixed with other constituents or combined with other materials depending on the application. Examples of the form include a variety of forms including powders, powder-containing dispersions, powder-containing particles, powder-containing coatings, powder-containing fibers, powder-containing papers, powder-containing plastics, powder-containing films, powder-containing aerosols and the like. If necessary, the antimicrobial agent may be used in combination with a variety of additives or materials such as other antimicrobial agents, deodorants, antiviral agents, anti-allergic agents, photocatalysts, flame retardants, anticorrosion agents, fertilizers, construction materials and the like.

The silver-based inorganic antimicrobial agent of the present invention may be mixed with a variety of additives to improve kneading processability into resin or other physical properties of resins. Specific examples thereof include pigments such as zinc oxide or titanium oxide, inorganic ion exchangers such as zirconium phosphates or zeolites, dyes, antioxidants, light resistance stabilizers, flame retardants, antistatic agents, defoaming agents, impact resistance reinforcing agents, glass fibers, lubricants such as metal soaps, moisture resistance agents and extenders, coupling agents, nucleating agents, flow modifiers, deodorants, wood powders, antifungal agents, antifouling agents, anticorrosion agents, metal powders, UV absorbers, UV blockers and the like.

An antimicrobial resin composition can be easily obtained by mixing the silver-based inorganic antimicrobial agent of the present invention with a resin. The type of the resin that can be used is not particularly limited and may be any of a natural resin, a semi-synthetic resin, and a synthetic resin, and may be either a thermoplastic resin or a thermosetting resin. Specifically, the resin may be any one of a molding resin, a fiber resin, and a rubber resin, and examples of the resin include molding or fiber resins such as polyethylene, polypropylene, vinyl chloride, ABS resins, AS resins, MBS resins, nylon resins, polyester, polyvinylidene chloride, polystyrene, polyacetal, polycarbonate, PBT, acrylic resins, fluorine resins, polyurethane elastomers, polyester elastomers, melamine resins, urea resins, tetrafluoroethylene resins, unsaturated polyester resins, rayon, acetate, acrylic, polyvinyl alcohol, cupro, triacetate, and vinylidene; and rubber resins such as natural rubbers, silicone rubbers, styrene butadiene rubbers, ethylene propylene rubbers, fluorine rubbers, nitrile rubbers, chlorosulfonated polyethylene rubbers, butadiene rubbers, synthetic natural rubbers, butyl rubbers, urethane rubbers, and acrylic rubbers. In addition, antimicrobial fibers may be prepared by combining the silver-based inorganic antimicrobial agent of the present invention with fibers such as natural fibers.

The mix proportion of the silver-based inorganic antimicrobial agent of the present invention into the antimicrobial resin composition is preferably 0.1 to 50 parts by mass and is more preferably 0.3 to 20 parts by mass, with respect to 100 parts by mass of the antimicrobial resin composition. When the proportion is lower than 0.1 parts by mass, improvement in the duration of antimicrobial property of the antimicrobial resin composition may be insufficient. Meanwhile, even if the proportion is higher than 50 parts by mass, the antimicrobial effects are not significantly improved and economic efficiency may be decreased and physical properties of resins may be considerably deteriorated.

A method for obtaining resin molded articles by mixing the silver-based inorganic antimicrobial agent of the present invention with a resin may be any one selected from methods known in the art. Examples of the method include (1) directly mixing a pellet-shaped resin or powder-type resin using an adhesive to facilitate adhesion of a silver-based inorganic antimicrobial agent powder to a resin, or a dispersant to improve dispersibility of the antimicrobial agent powder with a mixer, (2) molding the mixed composition thus obtained into pellets using an extrusion molding machine and mixing the molded material with another pellet-type resin, (3) molding the silver-based inorganic antimicrobial agent into pellets with a high concentration using a wax and mixing the pellet-shaped molded materials with another pellet-type resin, (4) dispersing the silver-based inorganic antimicrobial agent in a highly viscous liquid such as a polyol, followed by mixing, to prepare a paste-type composition and mixing the paste with a pellet-type resin and the like.

The molding of the antimicrobial resin composition may be carried out using any known processing techniques and machines depending on the characteristics of a variety of resins, the composition may be easily prepared in accordance with a mixing, incorporation or kneading method while heating and pressurizing or depressurizing at a suitable temperature or pressure, and the detailed operation thereof may be carried out using a common method and the composition may be molded into a variety of forms such as a lump, sponge, film, sheet, filament or pipe form or a combination thereof.

The inorganic antimicrobial composition can be obtained by mixing the silver-based inorganic antimicrobial agent of the present invention with an inorganic material with a binding property such as colloidal silica or silicate or other inorganic materials such as antimicrobial glass. Inorganic antimicrobial products can be manufactured using colloidal silica, silicate or the like by molding the composition, followed by drying or baking, thereby firmly sintering. These products exhibit superior heat resistance or solvent resistance.

The use type of the silver-based inorganic antimicrobial agent of the present invention is not particularly limited and is not limited to mixing with resin molded articles or polymer compounds. The antimicrobial agent may be mixed with other components or combined with other materials, depending on whether the application requires antifungal properties, antialgal properties or antimicrobial properties. For example, the antimicrobial agent may be used in a variety of forms such as powder, powder dispersion, particulate, aerosol or liquid forms.

The silver-based inorganic antimicrobial agent of the present invention also exhibits superior long-lasting waterproofing and may thus be effectively utilized in applications associated with water contact. Examples thereof include filter materials for water purifiers, washable fiber products, pipes or tanks through which water passes or in which water is contained, kitchen appliances always in contact with water, toiletries, sponges and the like.

The silver-based inorganic antimicrobial agent of the present invention exhibits a superior pasteurizing property with respect to water coming into contact with the agent as well as excellent long-lasting waterproofing and is thus preferably used as a water processing material. When the silver-based inorganic antimicrobial agent of the present invention is used unchanged as a water processing material, the agent is superior, in that a water permeation property when the agent is filled in a column or the like and used is good, as compared to a silver-based inorganic antimicrobial agent containing a large amount of particulate component obtained by a conventional wet-preparation method. When the antimicrobial agent is dispersed in water and then separated and collected, sedimentation is rapid and the water permeation property is maintained and clogging is avoided, even in a case where it is mounted as a cake on a filter. The water processing material is the best application of the silver-based inorganic antimicrobial agent of the present invention.

In addition, the antimicrobial resin composition or the molded article thereof may be used as a water processing material. Since the silver-based inorganic antimicrobial agent of the present invention contains a small amount of particulate component, the composition can be molded in the form of a porous lump or film, and the molded article has a superior water permeation property and is easy to handle as a water processing material.

Applications

The silver-based inorganic antimicrobial agent of the present invention may be utilized in a variety of fields requiring antimold, antialgal and antimicrobial properties, such as electrical products, kitchen products, fiber products, house construction material products, toiletry products, paper products, toys, leather products, stationery and other products and the like.

More specifically, examples of the application include electrical products including dishwashers, dish dryers, refrigerators, washing machines, pots, televisions, PCs, radio cassette players, cameras, video cameras, water purifiers, rice cookers, vegetable cutters, registers, blanket dryers, FAXs, extractor fans, air conditioners and the like, and kitchen products including dishes, cutting boards, guillotines, trays, chopsticks, tea supply machines, thermos bottles, kitchen knives, ladle handles, fried egg turners, lunchboxes, paddles, bowls, draining racks, triangular food waste baskets, scouring brush containers, waste baskets, draining bags and the like.

The fiber products include shower curtains, cotton cottons, air conditioner filters, pantyhose, socks, wet towels, sheets, blanket covers, pillows, gloves, aprons, curtains, diapers, bandages, masks, sports wear and the like. The house construction material products include decorative laminates, wallpapers, floorboards, window films, knobs, carpets, mats, artificial marbles, balustrades, masonry joints, tiles, waxes and the like. In addition, bathroom products include toilet seats, bathtubs, tiles, chamber pots, diaper boxes, toilet brushes, bathtub covers, pumice stones, soap cases, bathroom chairs, garment baskets, showers, basins and the like. Paper products include wrapping paper, pill paper, drug boxes, sketch books, medical charts, notes, paper for folding and the like. The toys include dolls, stuffed toys, paper clays, blocks, puzzles and the like.

In addition, leather products include shoes, bags, belts, watch bands or the like, indoor parts, chairs, globes, straps and the like. Stationery includes ballpoint pens, mechanical pencils, pencils, erasers, crayons, paper, notebooks, flexible disks, rulers, sticky notes such as Post it (trade name), staplers and the like.

Other products include insoles, make-up cases, scouring brushes, make-up puffs, hearing aids, musical instruments, cigarette filters, sticky sheets for cleaning, strap grips, sponges, kitchen towels, cards, microphones, hairdressing products, vending machines, shavers, telephones, thermometers, stethoscopes, slippers, garment cases, tooth brushes, sands in sandpits, food package films, antimicrobial sprays, coatings and the like.

The zirconium phosphate salt-based silver-based inorganic antimicrobial agent of the present invention has crude particle sizes, as compared to silver-based inorganic antimicrobial agents obtained by conventional wet, hydrothermal and calcination methods and the like, and exhibits superior water permeation properties and enables easy separation from water, after water disposal when used as a water processing material in which pasteurization is performed through contact with water. In addition, when kneading into a processed resin product, since aggregation or the like may not occur and the silver-based inorganic antimicrobial agent can be easily exposed on the surface of molded articles, antimicrobial effects are readily exhibited on the surface. For this reason, antimicrobial effects can be easily exhibited by kneading into coatings or films with a specific film thickness, and into a part of a molded article.

EXAMPLES

Hereinafter, the present invention will be described with reference to examples and is not limited thereto.

The peak intensity (cps) at about $2\theta=20.2°$ C. measured with X-rays of 50 kV/120 mA by powder X-ray diffraction was measured from heights of diffraction peaks after the background was reduced using a powder X-ray diffraction analyzer using a copper target X-ray pipe as an irradiation source.

The median particle size was analyzed on a volume basis using a laser diffraction particle size distribution meter.

A minimal growth inhibition concentration (MIC, μg/ml) to *E. coli* was obtained by pour-culturing samples at concentrations of 1000, 500, 250, 125, 62.5 μg/ml on a heated and fused normal agar medium, inoculating *E. coli* on the solidified plate and measuring a minimal concentration, showing no proliferation.

Example 1

0.1 moles of basic zirconium carbonate containing 2.1% hafnium ($2ZrO_2.CO_2.H_2O$) composed of particles wherein a median particle size thereof was 16 μm and particles with a particle size of 10 μm to 17 μm were present at 99.9% or more on a volume basis of the total particles was suspended in 300 ml of deionized water and 0.28 moles of phosphoric acid was added thereto while stirring. A 20% aqueous solution containing 0.12 moles of sodium hydroxide was further added thereto, followed by heating at 2° C./min and aging at 95° C. for 2 hours. Then, the resulting precipitate was sufficiently washed until the electrical conductivity of the filtrate was about 300 μS, dried at 120° C., and then heated at 1,100° C. for 8 hours using an electric furnace, thus synthesizing a hexagonal zirconium phosphate powder. 20 g of this hexagonal zirconium phosphate was added to 100 ml of an aqueous solution containing 3.4 g of silver nitrate, followed by stirring at 60° C. for 2 hours. After 2 hours, the solid was separated by filtration using filter paper, and the filtrate was sufficiently washed until the electrical conductivity thereof was about 50 μS, and then dried at 120° C. The resulting silver-based inorganic antimicrobial agent could be easily crushed using a mortar and was identified as hexagonal zirconium phosphate by powder X-ray diffraction. The measurement results of the peak intensity (cps) at about $2\theta=20.2°$ by powder X-ray diffraction, median particle size, the content of particles with a size of 10 μm to 100 μm on a volume basis and minimum growth inhibition concentration using *E. coli* are shown in Table 1.

Example 2

0.1 moles of basic zirconium carbonate containing 2.1% hafnium ($2ZrO_2.CO_2.H_2O$) composed of particles wherein a median particle size thereof was 16 μm and particles of a particle size of 10 μm to 17 μm were present at 99.9% or more on a volume basis of the total particles was suspended in 300 ml of deionized water and 0.28 moles of phosphoric acid was added thereto while stirring. A 20% aqueous solution containing 0.12 moles of sodium hydroxide was further added thereto, followed by heating at 2° C./min and aging at 95° C. for 2 hours. Then, the resulting precipitate was sufficiently washed until the electrical conductivity of the filtrate was about 300 μS, dried at 120° C., and then heated using an electric furnace at 1,100° C. for 8 hours, thus synthesizing a hexagonal zirconium phosphate powder. 20 g of this hexagonal zirconium phosphate was added to 100 ml of a 0.1N aqueous nitric acid solution containing 3.4 g of silver nitrate, followed by stirring at 60° C. for 2 hours. After 2 hours, the solid was separated by filtration using filter paper, sufficiently washed until the electrical conductivity of the filtrate was about 50 μS, and then dried at 120° C. and further calcinated at 700° C. for 4 hours. The resulting silver-based inorganic antimicrobial agent could be easily ground using a mortar and was identified as hexagonal zirconium phosphate by powder X-ray diffraction. The measurement results of the peak intensity (cps) at about $2\theta=20.2°$ by powder X-ray diffraction, median particle size, the content of particles with a size of 10 μm to 100 μm on a volume basis and minimum growth inhibition concentration using *E. coli* are shown in Table 1.

Example 3

0.1 moles of basic zirconium carbonate containing 2.1% hafnium ($2ZrO_2.CO_2.H_2O$) composed of particles wherein a median particle size thereof was 24 μm and particles with a particle size of 10 μm to 29 μm were present at 99.9% or more on a volume basis of the total particles was suspended in 300 ml of deionized water and 0.27 moles of phosphoric acid was added thereto while stirring. A 20% aqueous solution containing 0.12 moles of sodium hydroxide was further added thereto, followed by heating at 2° C./min and aging at 95° C. for 2 hours. Then, the resulting precipitate was sufficiently washed until the electrical conductivity of the filtrate was about 300 μS, and dried at 120° C. After drying, a hexagonal zirconium phosphate powder was synthesized by heating using an electric furnace at 1,100° C. for 8 hours. 20 g of this hexagonal zirconium phosphate was added to 100 ml of an aqueous solution containing 3.4 g of silver nitrate, followed by stirring at 60° C. for 2 hours. After 2 hours, the solid was separated by filtration using filter paper, and the filtrate was sufficiently washed until the electrical conductivity thereof was about 50 μS, and then dried at 120° C. The resulting silver-based inorganic antimicrobial agent could be easily ground using a mortar and was identified as hexagonal zirconium phosphate by powder X-ray diffraction. The measurement results of the peak intensity (cps) at about $2\theta=20.2°$ by powder X-ray diffraction, median particle size, the content of particles with a size of 10 μm to 100 μm on a volume basis and minimum growth inhibition concentration using *E. coli* are shown in Table 1.

Example 4

0.1 moles of basic zirconium carbonate containing 2.1% hafnium ($2ZrO_2.CO_2.H_2O$) composed of particles wherein a median particle size thereof was 16 μm and particles with a particle size of 10 μm to 17 μm were present at 99.9% or more on a volume basis of the total particles was suspended in 300 ml of deionized water and 0.28 moles of phosphoric acid was added thereto while stirring. A 20% aqueous solution containing 0.11 moles of sodium hydroxide was further added thereto, followed by heating at 2° C./min and aging at 95° C. for 2 hours. Then, the resulting precipitate was sufficiently washed until the electrical conductivity of the filtrate was about 300 μS, and dried at 120° C. After drying, a hexagonal zirconium phosphate powder was synthesized by heating using an electric furnace at 1,100° C. for 8 hours. 20 g of this hexagonal zirconium phosphate was added to 100 ml of an aqueous solution containing 0.72 g of silver nitrate, followed by stirring at 60° C. for 2 hours. After 2 hours, the solid was separated by filtration using filter paper, and the filtrate was sufficiently washed until the electrical conductivity thereof was about 50 μS, and then dried at 120° C. The resulting silver-based inorganic antimicrobial agent could be easily ground using a mortar and was identified as hexagonal zirconium phosphate by powder X-ray diffraction. The measurement results of the peak intensity (cps) at about $2\theta=20.2°$ by powder X-ray diffraction, median particle size, the content of particles with a size of 10 μm to 100 μm on a volume basis and minimum growth inhibition concentration using *E. coli* are shown in Table 1.

Comparative Example 1

Particulate Silver-based Inorganic Antimicrobial Agent Using Hexagonal Zirconium Phosphate by Wet Method 0.2 moles of zirconium oxychloride containing 1.6% hafnium was dissolved in 300 ml of deionized water and 0.3 moles of phosphoric acid was added thereto while stirring. 0.1 moles of a potassium hydroxide was further added thereto in 20% of an aqueous solution, followed by heating to 98° C. and aging for 2 hours. Then, the resulting precipitate was sufficiently washed and dried at 120° C. After drying, a hexagonal zirconium phosphate was synthesized by heating using an electric furnace at 1,100° C. for 8 hours. The hexagonal zirconium phosphate was ground using a ball mill. 20 g of this hexagonal zirconium phosphate was added to 100 ml of an aqueous solution containing 0.72 g of silver nitrate, followed by stirring at 60° C. for 2 hours. After 2 hours, the solid was separated by filtration using filter paper, was sufficiently washed until the electrical conductivity of the filtrate was about 50 μS, and then dried at 120° C. The resulting silver-based inorganic antimicrobial agent was ground and was identified as hexagonal zirconium phosphate by powder X-ray diffraction. The measurement results of the peak intensity (cps) at about $2\theta=20.2°$ by powder X-ray diffraction, median particle size, the content of particles with a size of 10 μm to 100 μm on a volume basis and minimum growth inhibition concentration using *E. coli* are shown in Table 1.

Comparative Example 2

Crude Particle Silver-based Inorganic Antimicrobial Agent Using Hexagonal Zirconium Phosphate by Calcination Method 0.2 moles of zirconium oxide containing 1.6% hafnium, 0.3 moles of ammonium dihydrogen phosphate and 0.1 moles of potassium carbonate were mixed using a ball mill, and stepwise calcinated using an electric furnace at 200° C. for 4 hours, at 900° C. for 4 hours, at 1400° C. for 4 hours to synthesize hexagonal zirconium phosphate. The hexagonal zirconium phosphate was ground using a ball mill. 20 g of this hexagonal zirconium phosphate was added to 100 ml of an aqueous solution containing 0.72 g of silver nitrate, followed by stirring at 60° C. for 2 hours. After 2 hours, the solid was separated by filtration using filter paper, was sufficiently washed until the electrical conductivity of the filtrate was about 50 μS, and then dried at 120° C. The resulting silver-based inorganic antimicrobial agent was ground and was identified as hexagonal zirconium phosphate by powder X-ray diffraction. The measurement results of the peak intensity (cps) at about $2\theta=20.2°$ by powder X-ray diffraction, median particle size, the content of particles with a size of 10 μm to 100 μm on a volume basis and minimum growth inhibition concentration using *E. coli* are shown in Table 1.

Comparative Example 3

Zeolite-based Silver-based Inorganic Antimicrobial Agent 100 ml of an ion exchange solution containing 0.72 g of silver nitrate was added to 20 g of commercially available A-type zeolite, followed by stirring at 60° C. for 2 hours to support silver. The resulting silver-based inorganic antimicrobial agent was ground and the measurement results of median particle size, the content of particles with a size of 10 μm to 100 μm on a volume basis and minimum growth inhibition concentration using *E. coli* are shown in Table 1. In addition, no peak was present at a position of $2\theta=20.2°$ observed by powder X-ray diffraction.

Comparative Example 4

A hexagonal zirconium phosphate powder in which the hexagonal zirconium phosphate obtained in the same manner as Example 3 was not subjected to silver ion exchange treatment was used for Comparative Example 4. The measurement results of the peak intensity (cps) at about $2\theta=20.2°$ by powder X-ray diffraction, median particle size, the content of particles with a size of 10 μm to 100 μm on a volume basis and minimum growth inhibition concentration using *E. coli* are shown in Table 1.

Comparative Example 5

A hexagonal zirconium phosphate powder was synthesized in the same manner as Example 1 except that basic zirconium carbonate containing 2.1% hafnium ($2ZrO_2.CO_2.H_2O$) composed of particles wherein a median particle size thereof was 1.9 μm and particles with a particle size of 5 μm to 100 μm were present at 77% on a volume basis of the total particles was used. Silver ion exchange treatment was performed to obtain a silver-based inorganic antimicrobial agent. The MIC of the antimicrobial agent was measured and the results are shown in Table 1.

Comparative Example 6

A hexagonal zirconium phosphate powder was synthesized in the same manner as Example 1 except that basic zirconium carbonate containing 2.1% hafnium ($2ZrO_2.CO_2.H_2O$) composed of particles wherein a median particle size thereof was 77 μm and particles with a particle size of 5 μm to 100 μm were present at 73% on a volume basis of the total particles was used. Silver ion exchange treatment was performed to obtain a silver-based inorganic antimicrobial agent. The MIC of antimicrobial agent was measured and the results are shown in Table 1.

TABLE 1

|  | Peak intensity (cps) | Median particle size (μm) | Content of particles of 10 μm to 100 μm (%) | MIC (μg/ml) |
|---|---|---|---|---|
| Ex. 1 | 4200 | 20 | 96 | 50 |
| Ex. 2 | 4100 | 21 | 93 | 50 |
| Ex. 3 | 3900 | 24 | 92 | 50 |
| Ex. 4 | 4100 | 18 | 98 | 100 |
| Comp. Ex. 1 | 5500 | 0.9 | 0 | 50 |
| Comp. Ex. 2 | 3700 | 13 | 65 | 100 |
| Comp. Ex. 3 | — | 11 | 78 | 100 |
| Comp. Ex. 4 | 4100 | 23 | 92 | >3200 |
| Comp. Ex. 5 | 5100 | 2.4 | 21 | 50 |
| Comp. Ex. 6 | 2900 | 81 | 67 | 1600 |

Example 5

Evaluation of Antimicrobial Treatment by Passing of Industrial Water

The silver-based inorganic antimicrobial agents obtained in Example 1, Example 4 and Comparative Examples 1 to 3 were filled in a water purifier cartridge and industrial water having a mean bacteria number of about 94/ml was passed. A water passing state and the number of general bacteria in 1 ml of industrial water at 10 minutes after water passing were measured by a pour culturing method using a general agar medium and the results are shown in Table 2.

TABLE 2

|  | Water passing state | Number of general bacteria |
|---|---|---|
| Ex. 1 | Good | <1 |
| Ex. 4 | Good | <1 |
| Comp. Ex. 1 | Not passed | Not measured |
| Comp. Ex. 2 | Not passed | Not measured |
| Comp. Ex. 3 | Good | 4 |
| Comp. Ex. 4 | Good | 91 |
| Comp. Ex. 5 | Not passed | Not measured |

It could be seen that Comparative Examples 1, 2 and 5 containing more particulates could not pass water, while Examples 1 and 4 exhibited a good water permeation property and a high reduction effect on the number of general bacteria. The most preferred application of the inorganic antimicrobial agent of the present invention is application as a water processing material.

Example 6

Evaluation of Polypropylene Film

The silver-based inorganic antimicrobial agents obtained in Example 1, Example 4 and Comparative Examples 1 to 3 were added by a dry blend at a concentration of 1% with respect to a polypropylene resin without using any dispersing agent, and a film with a film thickness of about 30 μm was formed. On the other hand, for reference, a blank film containing no antimicrobial agent was prepared in the same manner as above. The resulting antimicrobial film was observed by the naked eye and the results are shown in Table 3. Furthermore, an antimicrobial test using *E. coli* and *Staphylococcus Aureus* was performed in accordance with a method of JIS Z2801 5.2 plastic product and the like to evaluate antimicrobial effects and the resulting antimicrobially active values are shown in Table 3.

TABLE 3

|  | Appearance | Antimicrobially active value E. coli | Antimicrobially active value Staphylococcus aureus |
|---|---|---|---|
| Ex. 1 | No variation | >5.2 | >4.1 |
| Ex. 4 | No variation | >5.2 | >4.1 |
| Comp. Ex. 1 | Presence of white spots in which antimicrobial agent particles aggregate | 1.1 | 1.1 |
| Comp. Ex. 2 | Presence of white spots in which antimicrobial agent particles aggregate | 2.3 | 2.9 |
| Comp. Ex. 3 | Yellowing | >5.2 | 3.4 |

It was seen that Comparative Example 1 and Comparative Example 2 exhibited white spots due to dispersion defects, and Comparative Example 3 exhibited yellowing of film, while Examples 1 and 4 exhibited no variation in appearance and superior antimicrobial effects. It was thought that Comparative Example 3 exhibited low stability of silver ions since it did not use hexagonal zirconium phosphate, and thus yellowing due to heat during film processing may occur.

Industrial Applicability

The silver-based inorganic antimicrobial agent of the present invention is made of crude particles and thus readily exhibits antimicrobial effects, when kneaded into coatings or films with a specific film thickness or a part of molded articles. In addition, the silver-based inorganic antimicrobial agent can pasteurize water when in contact with water as a water processing material and is easily separated from an aqueous solution by filtration or precipitation after treatment, thus being suitable for water treatment.

What is claimed is:

1. A silver-based inorganic antimicrobial agent containing hexagonal zirconium phosphate salt particles represented by Formula (A) below and having a particle size distribution wherein particles with a particle size of 10 μm to 100 μm are 90% or more on a volume basis:

$$Ag_aM_bZr_cHf_d(PO_4)_3 \cdot nH_2O \quad (A)$$

wherein M represents at least one ion selected from an alkali metal ion, an alkaline earth metal ion, an ammonium ion, a hydrogen ion and an oxonium ion, a, b, c and d are values satisfying $1.75<c+d<2.25$, and $a+b+4(c+d)=9$ provided that M is monovalent, and $a+2b+4(c+d)=9$ provided that M is divalent, and a, b, and c are positive numbers, d is zero or a positive number, and n is zero or a positive number of 2 or less.

2. The silver-based inorganic antimicrobial agent according to claim 1, wherein a median particle size based on volume measured by a laser particle size distribution meter is 10 to 50 μm.

3. A water processing material using the silver-based inorganic antimicrobial agent according to claim 1.

4. An antimicrobial product using the silver-based inorganic antimicrobial agent according to claim 1.

5. A water processing material comprising the silver-based inorganic antimicrobial agent, according to claim 2.

6. An antimicrobial product comprising the silver-based inorganic antimicrobial agent according to claim 2.